United States Patent [19]

Moyers et al.

[11] Patent Number: 5,750,991
[45] Date of Patent: *May 12, 1998

[54] METHOD AND APPARATUS FOR FORMING MULTIDIMENSTIONAL ATTENUATION CORRECTION DATA IN TOMOGRAPHY APPLICATIONS

[75] Inventors: J. Clifton Moyers, Oak Ridge; Ronald Nutt; William F. Jones, both of Knoxville, all of Tenn.

[73] Assignee: CTI Pet Systems, Inc., Knoxville, Tenn.

[*] Notice: The term of this patent shall not extend beyond the expiration date of Pat. No. 5,471,061.

[21] Appl. No.: 563,268

[22] Filed: Nov. 27, 1995

Related U.S. Application Data

[63] Continuation-in-part of Ser. No. 210,960, Mar. 21, 1994, Pat. No. 5,471,061, which is a continuation-in-part of Ser. No. 37,303, Mar. 26, 1993, Pat. No. 5,296,708.

[51] Int. Cl.⁶ ................................................ G01T 1/161
[52] U.S. Cl. ........................ 250/363.03; 250/363.04
[58] Field of Search .................... 250/363.03, 363.04, 250/363.09

[56] References Cited

U.S. PATENT DOCUMENTS 3,171,101  2/1965  Hounsfield ............................ 340/174
3,230,388  1/1966  Hounsfield ............................ 307/88.5

(List continued on next page.)

FOREIGN PATENT DOCUMENTS 0129780  10/1980  Japan ................................. 250/363.03
9003722   7/1990  WIPO .

OTHER PUBLICATIONS

Improved Spect Using Simultaneous Emmission and Transmission Tomograph Bailey et al The Journal of Nuclear Medicine vol. 28 No. 5 5/87 pp. 844–851.

"3D PET Using a Conventional Multislice Tomography w/o Septa" Cherry et al., Journal of Computer Asst'd Tomography, Jul./Aug. (cc w/parent).

(List continued on next page.)

Primary Examiner—David P. Porta
Assistant Examiner—Richard Hanig
Attorney, Agent, or Firm—Pitts & Brittian P.C.

[57] ABSTRACT

A method and apparatus for producing radioactive transmission measurements to form multi-dimensional attenuation correction data with a point source of radiation, such as required in positron emission tomography applications. This involves the passing of the point source proximate the face of a selected each of the tomograph units for the formation of a 3-D image, or a selected portion of the tomograph units for a 2-D image. As such, attenuation data, transmission data, detector performance data, etc., can be obtained. This point source of radiation, in one embodiment, is rapidly circulated through a conduit that passes across each detector face under the influence of a transport fluid in, for example, an oscillatory motion to achieve a selected radiation field whereby calculation of transmission measurements within a body positioned within the tomograph scanner is achieved. When not being circulated, the radiation source is held within a shield. Circulation of the transport fluid, typically a hydraulic fluid, is typically accomplished using a positive displacement pump. Position sensors are used to monitor the movement of the source in the conduit as well as its position within the shield. Disconnect units permit removal of the radiation source, as contained in the shield, from the system without accessing any other portions of the system. In another embodiment, the point source is a CT device.

21 Claims, 7 Drawing Sheets

U.S. PATENT DOCUMENTS

| | | | |
|---|---|---|---|
| 3,371,325 | 2/1968 | Hounsfield | 340/174 |
| 3,778,614 | 12/1973 | Hounsfield | 250/362 |
| 4,743,764 | 5/1988 | Casey et al. | 250/363 S |
| 5,008,822 | 4/1991 | Brunnett et al. | 364/413.21 |
| 5,296,708 | 3/1994 | Moyers et al. | 250/363.03 |
| 5,471,061 | 11/1995 | Moyers et al. | 250/363.03 |

OTHER PUBLICATIONS

"A High Performance Detector Electronic System for PET", J. Moyers, Jr. Thesis presented to UTK, May, 1990, (cc w/parent file).

"PET & Audiography", Phelps, et al., Raven Press, 1986 (Copy not available).

"The Atomic Nucleus", Evans, R.D., Kreiger, 1955 (Copy not available).

DeKemp, R.A., "Attenuation Correction in Positron Emmission Tomography Using Single Photon Transmission Measurement", Master's Thesis, McMaster University, Ontario, Canada.(Sep. 1992).

Derenzo, S.E., H. Zaklad, T.F. Buding. "Analytical Study of a High–Resolution Positron Ring Detector System for Transaxial Reconstruction Tomography", *Journal of Nuclear Medicine*, vol. 16, No. 12, 1166–1173 (1975).

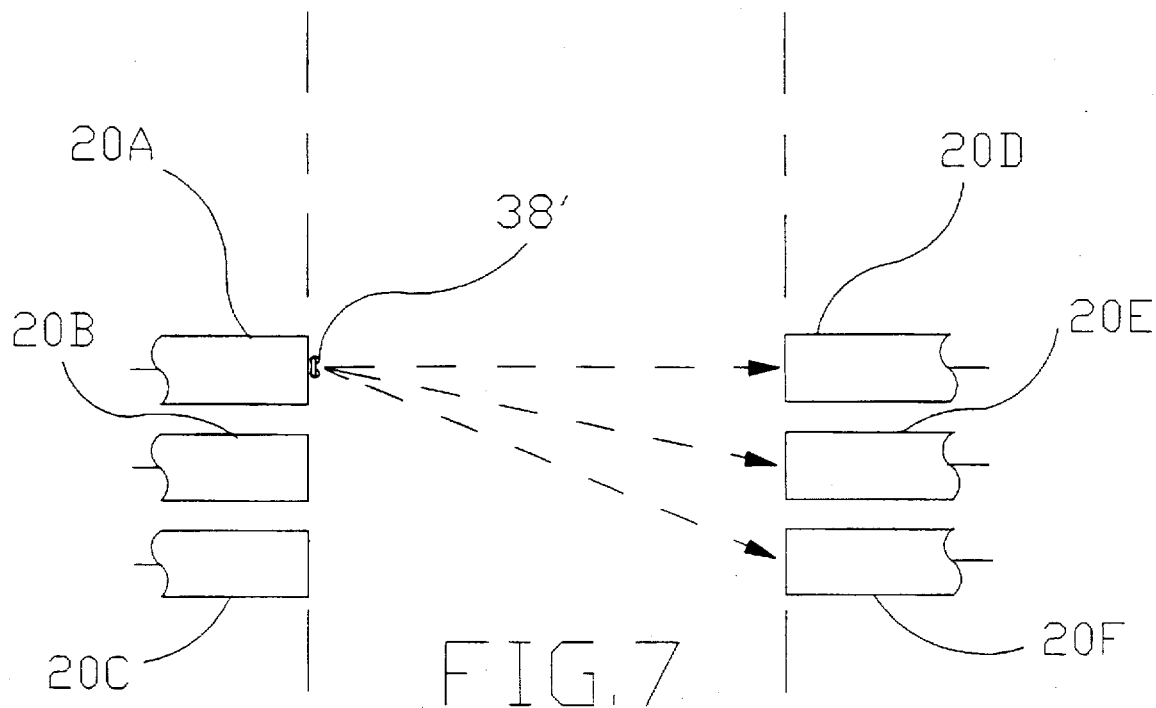
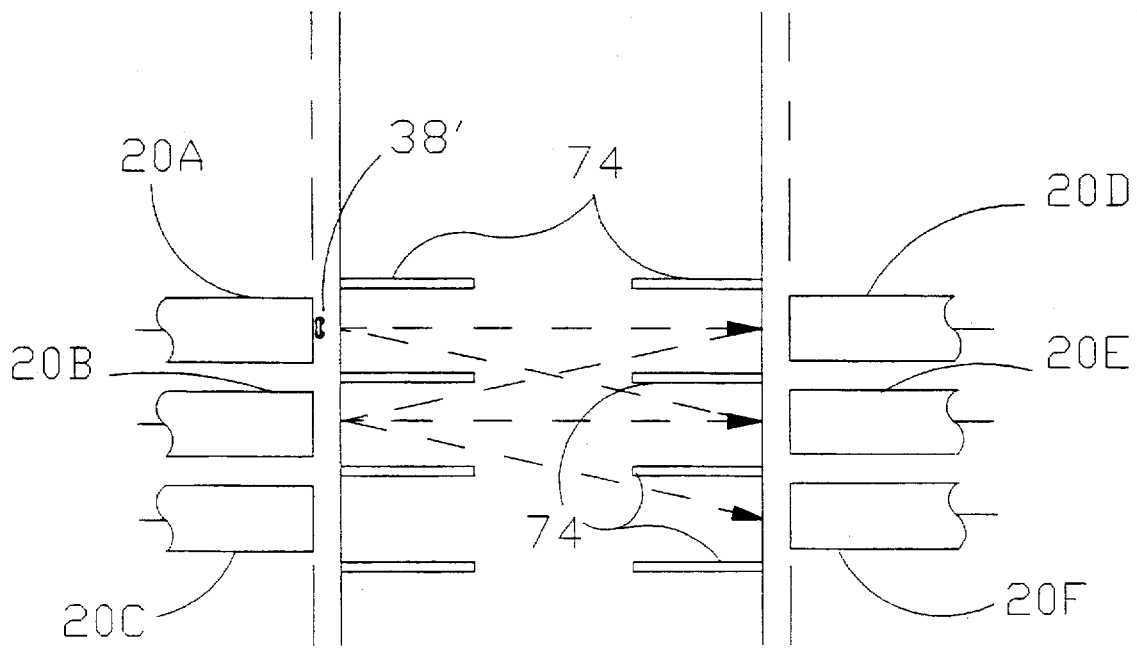

METHOD AND APPARATUS FOR FORMING MULTIDIMENSTIONAL ATTENUATION CORRECTION DATA IN TOMOGRAPHY APPLICATIONS

This application is a continuation in part and discloses and claims subject matter disclosed in our earlier filed pending application, Ser. No. 08/210,960, filed on Mar. 21, 1994, which issued into U.S. Pat. No. 5,471,061 on Nov. 28, 1995, and which is a continuation in part and disclosed and claimed subject matter in our earlier filed application, Ser. No. 08/037,303 filed on Mar. 26, 1993, which issued into U.S. Pat. No. 5,296,708 on Mar. 22, 1994.

TECHNICAL FIELD

The present invention relates generally to a method and apparatus for the transmission measurement to form a 3-D image for tomography applications, and more particularly to a method and apparatus for rapidly moving a point source of radiation past each detector of the tomograph apparatus together with determining the position of that source. Although described specifically for obtaining transmission attenuation in positron emission tomography, the method and apparatus is applicable for various purposes in other tomograph devices.

BACKGROUND ART

Positron Emission Tomography (PET) has gained significant popularity in nuclear medicine because of the ability to non-invasively study physiological processes within the body. PET is the most sensitive, and exhibits the greatest quantification accuracy, of any nuclear medicine imaging instrument available at the present time. Applications requiring this sensitivity and accuracy include those in the fields of oncology, cardiology and neurology.

Using compounds such as $^{11}$C-labeled glucose, $^{18}$F-labeled glucose, $^{13}$N-labeled ammonia and $^{15}$O-labeled water, PET can be used to study such physiological phenomena as blood flow, tissue viability, and in vivo brain neuron activity. These neutron deficient compounds interact with free electrons in the body area of interest, resulting in the annihilation of the positron. This annihilation yields the emission of a pair of photons (gamma rays) approximately 180 degrees (angular) apart. A compound having the desired physiological affect is administered to the patient, and the radiation resulting from annihilation is detected by a PET tomograph. After acquiring these annihilation "event pairs" for a period of time, the isotope distribution in a cross section of the body can be reconstructed.

PET data acquisition occurs by detection of both photons emitted from the annihilation of the positron in a coincidence scheme. Due to the approximate 180 degree angle of departure from the annihilation site, the location of the two detectors registering the "event" define a chord passing through the location of the annihilation. By histogramming these lines of response (the chords), a "sinogram" is produced that may be used by a process of back-projection to produce a two dimensional image of the activity. Detection of these lines of activity is performed by a coincidence detection scheme. A valid event line is registered if both photons of an annihilation are detected within a coincidence window of time. Coincidence detection methods ensure (disregarding other second-order effects) that an event line is histogrammed only if both photons originate from the same positron annihilation.

A recent, likely to become dominant, advance in PET acquisition methods is the method of data collection referred to as 3-D acquisition. In the traditional (2-D) acquisition of a modern PET tomograph, an expensive (usually tungsten) collimator known as a septa is placed between the object within the field-of-view and the discrete axial rings of detectors. This septa limits the axial angle that a gamma ray can impinge on a detector, typically limiting the number of axial rings of detectors that a given detector in a specific ring can form a coincidence with to three; one ring toward the front of the tomograph from the given detector's ring, the same ring that the detector is within, and the one ring toward the rear of the tomograph from the given detector's ring. The methodology of 3-D acquisition removes the septa and allows a given detector to be in coincidence with detectors from all other detector rings. Not only does 3-D acquisition allow removal of the very expensive septa from the tomograph, but it also affects a significant increase in tomograph efficiency.

Another tomography diagnostic system is that known as single photon emission computed tomography (SPECT) which is very similar to PET. The distinction is that only a single photon from the annihilation within the patient is detected. Otherwise, the apparatus is substantially like that of the PET system.

In computed axial tomography (CAT, or now also referred to as CT), an x-ray source is caused to be passed around a patient. Detectors around the patient then respond to x-ray transmission through the patient to produce an image of an area of study.

The details of carrying out a PET study are given in numerous publications. Typically, the following references provide a background for PET. These are incorporated herein by reference for any of their teachings.

1. M. E. Phelps, et al.: "Positron Emission Tomography and Audiography", Raven Press, 1986;

2. R. D. Evans: "The Atomic Nucleus", Kreiger, 1955;

3. J. C. Moyers: "A High Performance Detector Electronics System for Positron Emission Tomography", Masters Thesis, University of Tennessee, Knoxville, Tenn., 1990;

4. U.S. Pat. No. 4,743,764 issued to M. E. Casey, et al, on May 10, 1988;

5. R. A. DeKemp: "Attenuation Correction in Positron Using Single Photon Transmission Measurement", Masters Thesis, McMaster University, Hamilton, Ontario, Canada;

6. S. R. Cherry, et al.: "3-D PET Using a Conventional Multislice Tomograph Without Septa", Jl. C. A. T., 15(4) 655–668.

Both SPECT and CAT (or CT) systems are also well known to persons skilled in the art.

In order to achieve maximal quantitative measurement accuracy in tomography applications, an attenuation correction must be applied to the collected emission data. In a PET system, for example, this attenuation is dependent on both the distance the gamma ray must travel before striking the detector, and the density of the attenuating media in the path of travel. Depending on the location of the annihilation within the patient's body, large variations in attenuating media cross section and density have to be traversed. If not corrected for, this attenuation causes spatial variant inaccuracies in the images that degrade the desired accuracy. As an example, for a cardiac study the attenuation is highest in the line of responses (LORs) passing through the width of the torso and arms, and attenuation is lowest in the LORs passing through the front and back of the chest.

Typically, the attenuation correction data in PET systems is produced by either: shape fitting and linear calculations using known attenuation constants, these being applicable to symmetric well-defined shapes such as the head and torso below the thorax (calculated attenuation); or through the measurement of the annihilation photon path's attenuation using a separate transmission scan (measured attenuation). The use of calculated attenuation correction, which introduces no statistical noise into the emission, can be automated for simple geometries such as the head, and is the most prominent method used for brain studies. However, complexities in the attenuation media geometry within the chest have prevented the application of calculated attenuation from being practical for studies within this region of the body. Accordingly, transmission scanning has been utilized.

The total attenuation of a beam along a LOR through an object is equal to the attenuation that occurs for the two photons from an annihilation. Thus, the emission attenuation along the path can be measured by placing a source of gamma rays on the LOR outside of the body and measuring attenuation through the body along this line. It has been the practice to accomplish this attenuation measurement by placing a cylindrical positron emitter "sheet" within the PET's field of view (FOV) but outside of the region (the object) to be measured. By calculating the ratio of an already acquired blank scan (no object in the FOV) to the acquired transmission scan, variations in this ratio data represent the desired measured attenuation. This data is then applied to the emission data after a transmission scan of the object to correct for the spacial variations in attenuation.

There are two types of emitter units conventionally utilized in PET transmission scan data collection, both of which form a "sheet" of activity to surround the patient. One involves the placement of rings of activity aligned with detector rings around the inner face of the septa (see FIG. 1). The second type utilizes the rotation of one or more axially-oriented rods of activity in a circular path just inside the inner face of the septa (see FIG. 2).

The first of these two emitter systems (the ring source method) significantly reduces the sensitivity of the tomograph due to the close source-proximity dead time effects of the source activity on all of the detectors. Further, removal of this assembly is either performed manually by facility personnel or by a complex automated (more recent) mechanical assembly. Large, cumbersome, out of the FOV shielding is required for storage of the automated source when not in use, adding to the depth of the tomograph tunnel and, thus increasing incidence of patient claustrophobia. The second type of emitter, using rotating source(s) suffers from the above-mentioned problems and also, due to the shielding requirements, reduces the patient tunnel diameter, further increasing patient claustrophobia symptoms.

Both of the above automated source transportation methods suffer from high mechanical component cost and from low sensitivity. Due to the dead-time-induced reduction in tomograph sensitivity, lengthy acquisitions are required in order to achieve usable low noise transmission scan data.

Accordingly, it is an object of the present invention to provide a method and apparatus for rapidly moving a point source of radiation within a selected geometry to form attenuation correction data of radiation transmission measurements for correcting an emission data set, which may then be used to form an image within that geometry.

It is also an object of the present invention to provide a system that reduces the time of determining information in tomography scans.

It is another object of the present invention to provide an improved radiation emitter for carrying out attenuation data acquisition for use in obtaining increased accuracy in PET scans.

Another object of the present invention is to provide for the controlling of a position of a point source of radiation and for determining that position so as to generate multi-dimensional attenuation correction data of radiation transmission.

It is still another object of the present invention to provide a radiation source of substantially increased activity that can be used in tomography applications.

A further object of the present invention is to provide an improved radiation emitter that requires no mechanical motion within tomograph units, such as the PET unit, but accomplishes emission of radiation uniformly covering all detector coverage in cylindrical regions within the unit.

Another object of the present invention is to provide a method and apparatus for rapidly moving a point source of radiation within a selected geometry to form attenuation correction data of radiation transmission measurements for correcting an emission data set, wherein the point source of radiation is a CT scanner.

These and other objects of the present invention will become apparent upon a consideration of the drawings forming a part of the disclosure of the invention, together with a complete description thereof that follows.

DISCLOSURE OF THE INVENTION

In accordance with the present invention, there is provided a method and apparatus for causing a point source of radiation to rapidly move in a selected path around or adjacent an object being subject to a tomography scan to generate multi-dimensional attenuation correction data of radiation transmission through that selected path. This system utilizes substantially no moving components within the region of the object and thus substantially reduces cost associated with obtaining transmission data. The system utilizes a point source which may be carried within a tubing placed adjacent the surface of radiation detector faces such that the point source is passed adjacent each detector face or which may be a CT device carried on a single rotational support with the PET or SPECT device. In the first instance, the point source of a selected shape, which typically can be a sphere or a small cylinder, and is carried within a transport fluid typically moved by a positive displacement pump from a shielded position, through the tubing a selected number of times, and then returned to a storage shield. Typically the source is repetitively passed in an oscillatory manner through the tubing. Thus, the origination of the radiation from the point source can be controlled so as to direct radiation across the tomograph apparatus volume and through the object, with the conventional detectors being used to determine transmission data. In one embodiment of the invention for use in PET systems, the tubing is formed into a cylindrical helix and the transmission data is used to obtain photon attenuation data. In an alternate embodiment, the tubing is formed into a substantially linear configuration such that the point source is moved in a direction substantially parallel to the longitudinal axis of the tomograph apparatus. In the embodiment wherein the point source is a CT device, the tomograph device includes two banks of detectors on opposite sides of a ring. Gaps are defined between the banks of emission tomograph detectors. In one gap is positioned a bank of CT detectors. An X-ray generator is positioned to generate X-rays and direct the same through the opposing gap and the patient toward the bank of X-ray detectors. The CT device and detectors are stationary with respect to the emission tomograph device such that both the emission tomograph device and the CT device simultaneously acquire data.

BRIEF DESCRIPTION OF THE DRAWINGS

FIG. 7 is a schematic drawing of the alternate embodiment shown in FIG. 5 showing the impingement of radiation from the point source on a group of oppositely-disposed detectors.

FIG. 8 is a schematic drawing of the alternate embodiment shown in FIG. 5 including a group of collimators for narrowing the impingement of the radiation from the point source to a single oppositely-disposed detector.

BEST MODE FOR CARRYING OUT THE INVENTION

As discussed hereinafter, the present invention is applicable to producing multi-dimensional attenuation correction data of radiation transmission measurements for correcting an emission data set, which may be used to form an image within that geometry. It is especially applicable for many types of tomography applications, such as with PET or SPECT. The invention is described, for purposes of illustration, for a PET unit.

Figure 1:
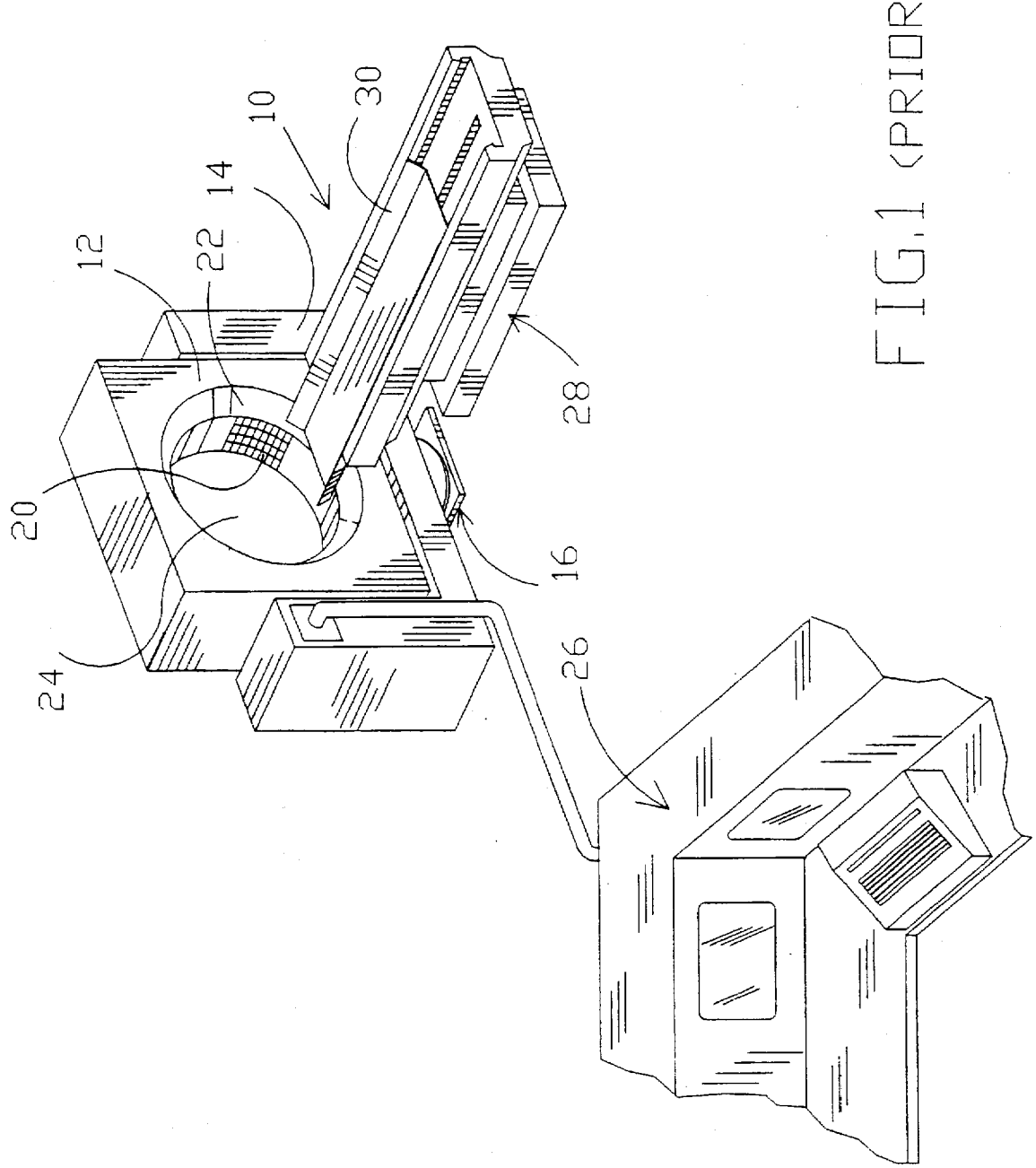
FIG. 1 is an isometric drawing illustrating a typical tomograph unit for a better understanding of the present invention.

For an understanding of a tomograph unit, and particularly a PET unit, reference is made to FIG. 1 where such unit is indicated generally at 10. In general, this unit 10 includes a gantry 12 of conventional design mounted upon a U-shaped mounting bracket 14 supported on a base 16. Detectors 20 for diagnostic imaging operations are carried in a cylindrical array on a ring 22, with the faces of the detectors 20 forming a cylindrical opening 24 for receiving a selected portion of a patient's body. Signal outputs from the detectors 20 are carried to a monitoring station 26 for analysis and display in a typical manner. This station 26 contains processing means for producing attenuation correction data and for combining this attenuation correction data with normal scan data of the PET unit. The unit includes a patient bed 28, which includes a sliding carriage 30, for moving the selected body portion into and out of the opening 24 in a conventional manner.

Figure 2:
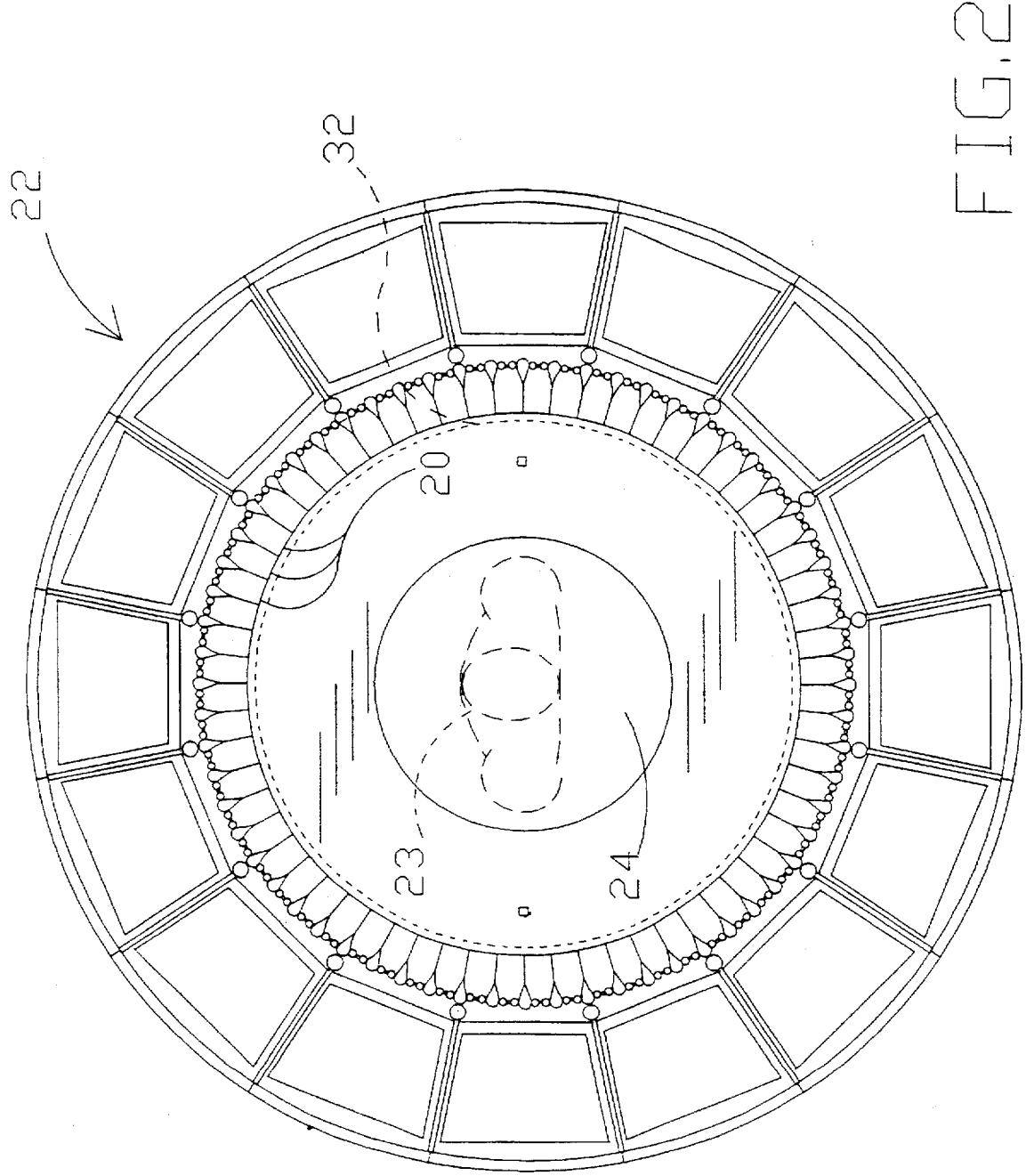
FIG. 2 is a cross-sectional view of a typical PET tomograph unit illustrating placement of detectors relative to an object, together with the placement of the point source of the present invention in the PET unit embodiment.

FIG. 2 is a cross-sectional view of the aforementioned ring 22 with the detector units 20 mounted thereon. This figure illustrates the position of a patient 23 as located on a central axis of the cylindrical array of detectors 20. This geometric arrangement is such as to generate the positron radiation from within the patient to impinge upon the various detectors 20 for achieving PET scan data. The prior devices for achieving attenuation data (rings of radiation or rotating radiation sources) were placed adjacent this cylindrical surface defined by the detectors 20. This is the same location, as indicated at 32, for the location of the present invention when applied to a PET unit.

Figure 3:
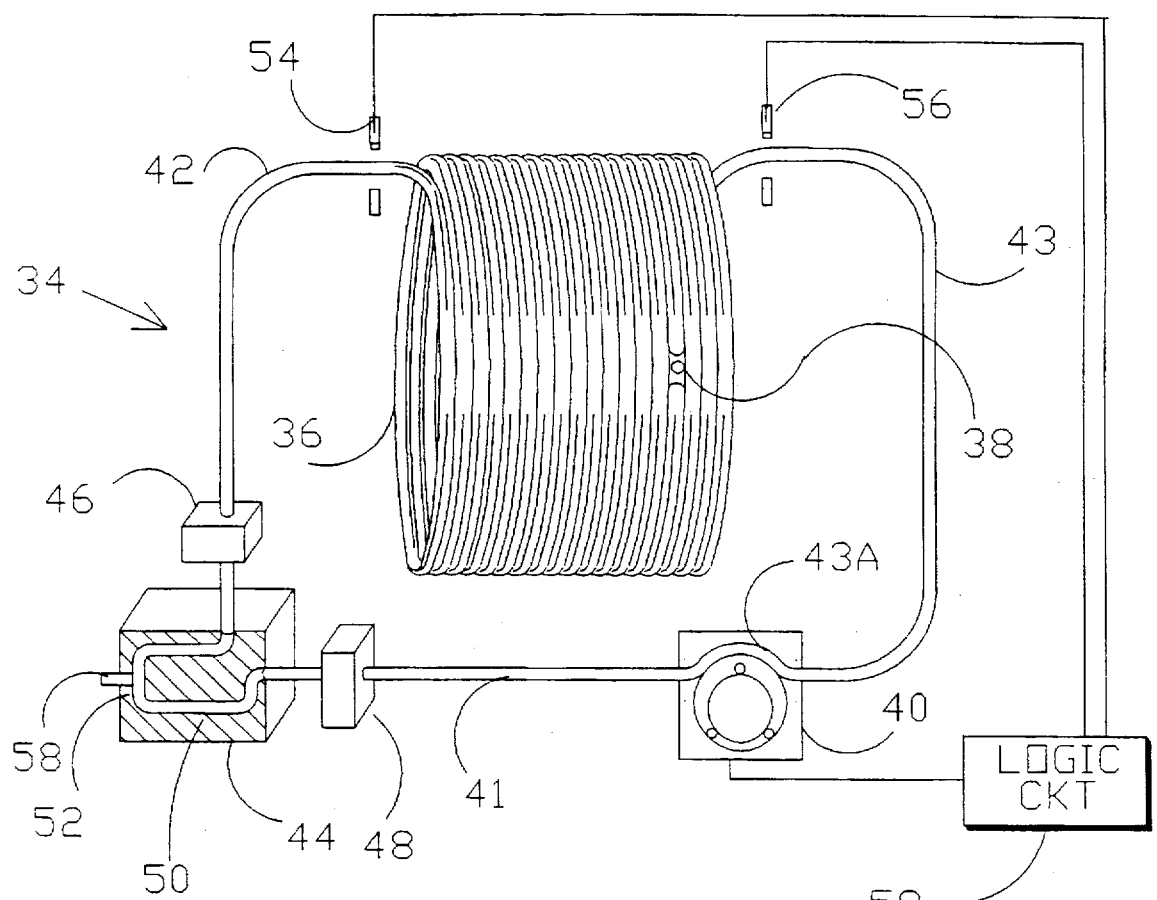
FIG. 3 is a schematic drawing illustrating the system for producing a cylindrical sheet of radiation for attenuation data generation according to the one embodiment of the present invention.

A schematic diagram of one embodiment of the present invention, as adapted for PET-type tomography, is shown at 34 in FIG. 3. A helix 36 formed from a suitable substantially rigid tubing forms a cylindrical unit dimensioned to be received in the location 32 of FIG. 2. This tubing can be "potted" with a suitable material (e.g., a low radiation attenuation plastic) into a solid structure so as to maintain its geometry. The interior dimension of the tubing of the helix is chosen to receive a point source radiation emitter unit 38. The desired source of radiation (e.g., gamma rays) can be, for example, either a small sphere or a small cylinder. It will be understood that the interior shape of the tubing is chosen to be compatible with the configuration of the point source of radiation. The spiral is typically formed from polyvinyl chloride (PVC) tubing or similar material exhibiting low attenuation to the selected radiation, and has an interior diameter typically about 3 mm. The external diameter of the tubing, and the pitch of the helix, is chosen so that the point source when within a location within the tubing passes past an individual one of the detector faces, with each detector face "seeing" the point source. The helix diameter is typically about 90 cm which is the diameter of the PET system inside the faces of the detectors. Typically the source 38 is $^{68}$Ge encapsulated in a gold enclosure which produces positrons like those that are emitted during the annihilation within the patient's body. Since gold is rather easily abraded, an outer hard coating of plastic or other low attenuation material is usually applied over the gold layer. Of course, it will be understood that other types of radiation, and sources for that radiation, can be utilized in the present invention.

This point source emitter unit is carried through the system in a suitable transport fluid. Preferably, this transport fluid is substantially non-compressible and thus is a liquid such as ethylene glycol or other low attenuation liquids. The transport fluid is moved typically by a positive displacement pump 40 such as a peristaltic pump. Other substantially non-compressible low attenuation fluids that are resistant to radiation damage will be known to persons skilled in the art. This pump 40 is connected into a fluid circuit that includes tubing 41 and tubing 42 that leads from a source shield 44 to the entrance of the helix 36. Of course, for a peristaltic pump there is a short section of flexible tubing, as at 43A, for passage through the pump 40. Typically, the tubing sections are polyvinyl chloride (PVC). Further, other means of moving the transport fluid through the helix 36 will be known to persons skilled in the art.

The source shield 44 is formed from a high-Z material (e.g., lead) and completely surrounds the path of the source 38 therein. This shield 44 is preferably arranged such that, by using the disconnects 46, 48, the shield 44 containing the source 38 can be removed from the system. Further, the specific gravity of the source 38 is chosen to be slightly higher than that of the transport fluid such that the source 38 will be retained in the "loop" 50 formed within the shield 44, when desired, in the absence of transport fluid flow. In addition, a mechanical "stop" 52 is preferably located within the shield 44 to prevent inadvertent discharge of the source 38 therefrom. This arrangement thus requires fluid circulation only during desired movement of the source 38.

In order to ascertain locations of the source 38 during movement or during positioning within the shield 44, the present system is typically provided with position sensors: sensor 54 is located at the entrance to the helix 36; sensor 56 is located at the exit from the helix 36; and sensor 58 is located within the shield 44 at the "park" position. These can be, typically, optical sensors when the tubing of the helix 36 is substantially transparent. For example, sensors 54 and 56 determine when the source 38 enters and reaches the exit of the helix 36, respectively. This prevents leaving the source 38 stationary within the helix 36. Then sensor 58 ascertains that the source 38 has actually been returned to the shield 44.

Whenever attenuation data is desired, the mechanical stop 52 is withdrawn and operation of the pump 40 is initiated in a direction to cause the source 38 to be moved toward the entrance of the helix 36. This causes the source 38 to be withdrawn from the shield 44 and circulated through the helix 36 via tubing 42. The sensors 54, 56 ensure that complete passage through the helix 36 has occurred. Typically logic circuitry 59 associated with sensors 54, 56 causes reversal of the pump 40 forcing the source 38 in a reverse direction until detected by sensor 54. Again there is a reversal, with this oscillatory movement continuing for a selected number of times to assure desired statistical data. The source 38 then is returned to the shield 44 through tubing 42 due to continued operation of the pump 40 until it again reaches the mechanical stop 52, with the location being ascertained by sensor 58.

During the circulation of the source 38 through the helix 36, the conventional PET radiation detectors 20 (see FIGS. 1 and 2) record the received radiation, and these data are processed in a conventional signal processor known to those skilled in the art to obtain the attenuation data that then can be used by a signal processor to appropriately adjust scan data received on the basis of annihilation events within the patient's body. As stated above, this processing occurs within circuitry at the station 26.

Figure 4:
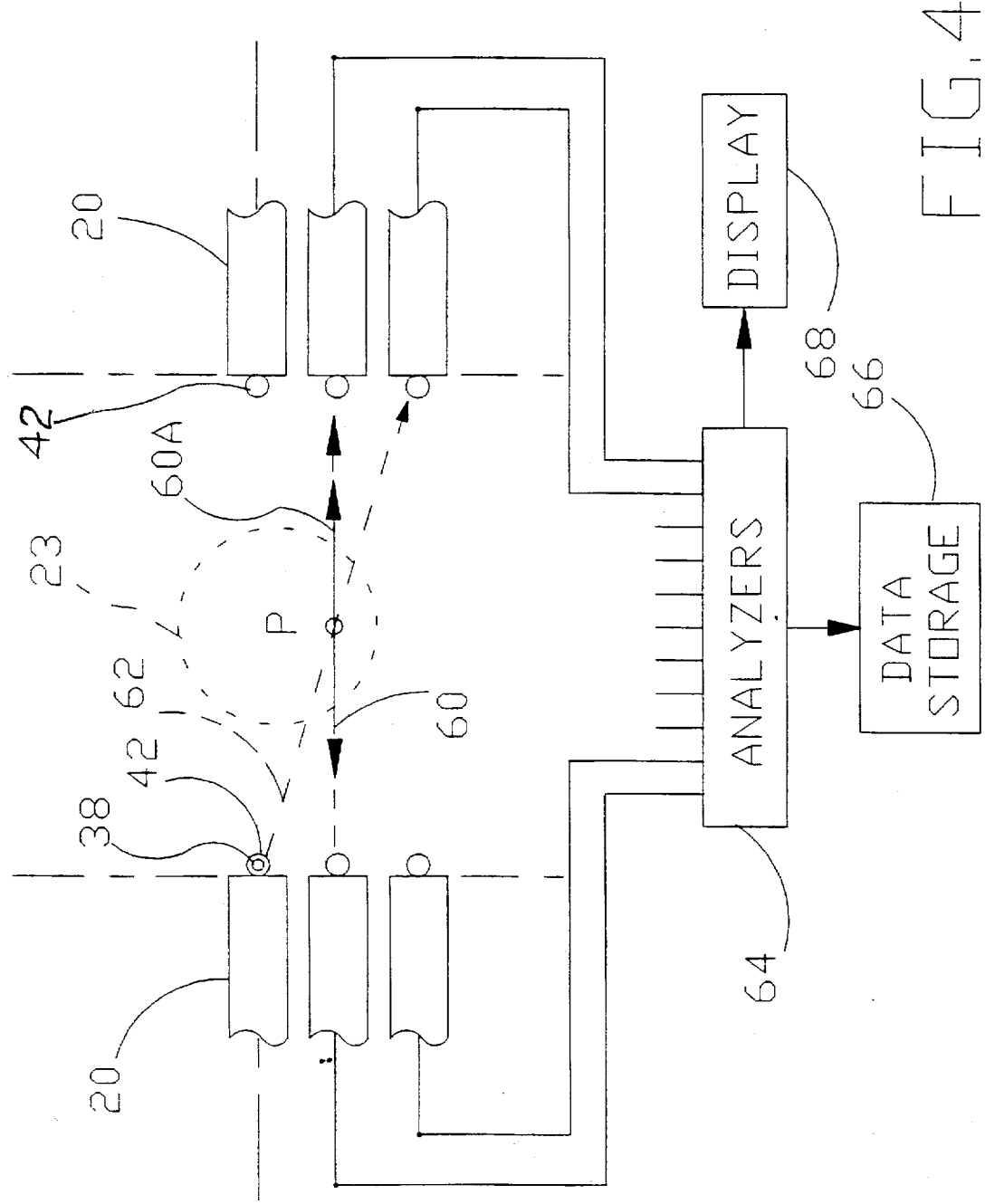
FIG. 4 is a schematic drawing showing the circuit whereby signals from detectors of tomograph units are processed to determine transmission, etc.

A schematic drawing depicting the receiving of radiation at detectors, and the processing of the signals, is contained in FIG. 4. In this drawing, several detectors 20 (of a multiplicity of detectors) on oppositely-disposed sides of the tomograph unit are depicted: it will be understood that there are many other detectors in a normal system. The tubing 42 passes the face of each of the detectors such that the point source of radiation 38 can pass over the detector face. Photon radiation 60, 60A (two photons as in the PET system) emanate from a point, P, of positron annihilation within a patient 23 in opposite directions toward the detectors 20. Further, photon radiation 62 from the point source passes through the patient 23, typically in the direction shown when the source is in the tubing at the left in the drawing. Signals from all of the detectors 20 are processed in pre-programmed analyzers 64, with the result being stored in storage unit 66 and depicted on a display unit 68. The processing of signals, their storage and their display are according to technology that will be known to those versed in the art.

Figure 5:
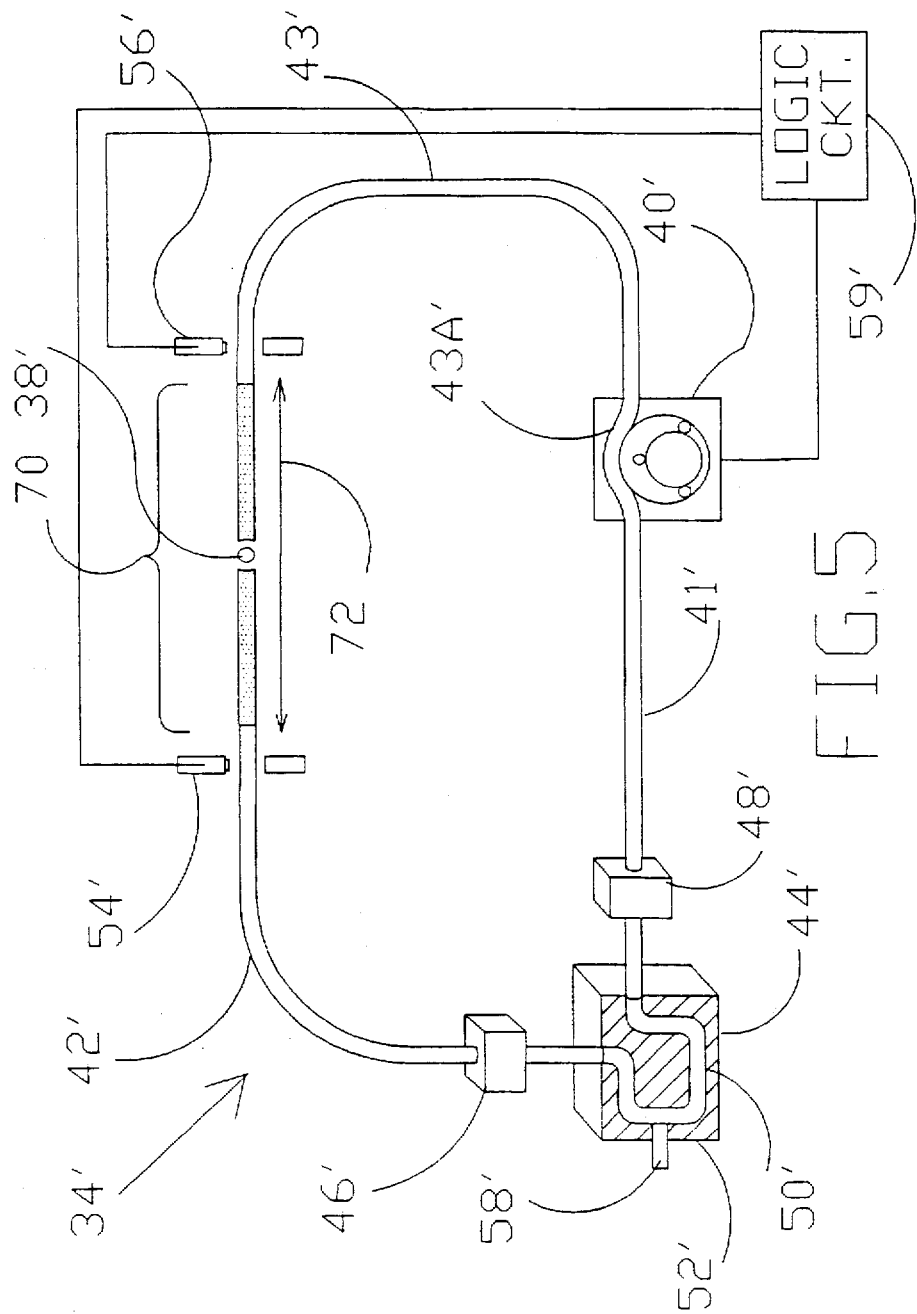
FIG. 5 is a schematic drawing illustrating an alternate embodiment of the system for producing a cylindrical sheet of radiation for attenuation data generation according to the one embodiment of the present invention.

A schematic diagram of an alternate embodiment of the present invention is shown at 34' in FIG. 5. In lieu of the helix 36 as formed in the embodiment illustrated in FIGS. 3 and 4, the tubing is configured to form a linear portion 70 between the sensors 54',56'. The linear portion 70 may be secured within the PET system proximate one row of detectors 20 in a direction parallel to the longitudinal axis of the ring 22. It is envisioned that the linear portion 70 may be secured proximate any one row of detectors 20, and further may be moved from one row of detectors 20 to another in order to allow the point source 38' to pass each detector face.

As in the previously described embodiment, whenever attenuation data is desired, the mechanical stop 52' is withdrawn and operation of the pump 40' is initiated in a direction to cause the source 38' to be moved toward the entrance of the linear portion 70. The sensors 54',56' ensure that complete passage through the linear portion 70 has occurred. The logic circuitry 59' associated with sensors 54',56' causes reversal of the pump 40' forcing the source 38' in a reverse direction until detected by sensor 54'. Again there is a reversal, with this oscillatory movement, as indicated by arrow 72, continuing for a selected number of times to assure desired statistical data. It is envisioned that, in an embodiment where the linear portion 70 is moved from one row of detectors 20 to another, a electromechanical device (not shown) may be incorporated to cause such movement. The electromechanical device may be actuated by the logic circuitry 59' such that after a selected number of oscillations of the point source 38' within the linear portion 70, the linear portion 70 may be moved to an adjacent or other selected row of detectors 20.

Figure 6:
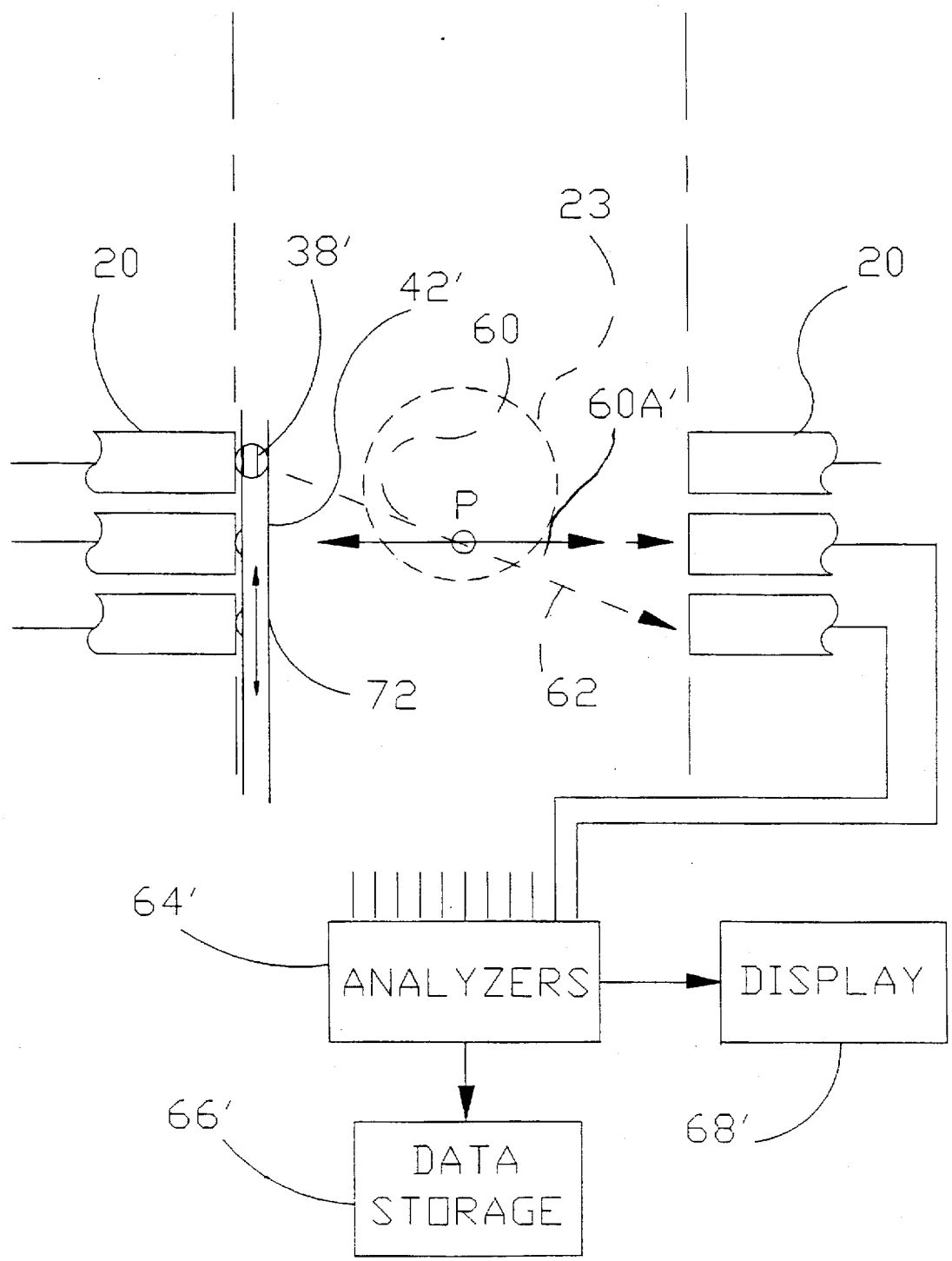
FIG. 6 is a schematic drawing of the alternate embodiment shown in FIG. 5 showing the circuit whereby signals from detectors of tomograph units are processed to determine transmission, etc.

A schematic drawing depicting the receiving of radiation at detectors in the alternate embodiment, and the processing of the signals, is contained in FIG. 6. The tubing 42' passes the face of each of one row of the detectors 20 such that the point source of radiation 38' can pass over each detector face in that row. Photon radiation 60, 60A (two photons as in the PET system) emanate from a point, P, of positron annihilation within a patient 23 in opposite directions toward the detectors 20. However, in this embodiment, only the photon radiation 60A directed toward the detector 20 opposite the linear portion 70 is considered. Further, photon radiation 62 from the point source passes through the patient 23. Signals from the detectors 20 are processed in pre-programmed analyzers 64, with the result being stored in storage unit 66 and depicted on a display unit 68.

As shown in FIG. 7, the radiation from the point source 38 is actually directed in a broad range of directions such that a plurality of detectors 20 are impinged upon. In this Figure, the tubing within which the point source 38 is passed has been omitted, as either configuration of tubing may be used. The point source 38 is depicted as being positioned in front of the detector 20A. In this case, the detector 20D directly across from the detector 20A which is being passed by the point source 38 will receive the greatest magnitude of radiation. As illustrated, with the point source 38 positioned in front of any detector 20, every other detector 20 will receive an amount of radiation dependent upon the distance away from the point source 38 and the portion of the human body 23 through which it passes. Thus, 2-dimensional data may be derived between any two detectors 20 positioned colinearly with the point source 38. A compilation of all of the 2-dimensional data yields a 3-dimensional image.

In an alternate embodiment as shown in FIG. 8, a plurality of collimators 74 may be placed to separate the individual rings of detectors 20 such that the radiation produced by the point source 38 is directed solely toward the detectors 20 in that same ring and the immediately adjacent rings. For example, as illustrated when the point source is in front of the detector 20A, only those detectors 20D,E are able to receive a signal. When the point source 38 is in front of the detector 20B, each of the detectors 20D,E,F receive a signal. Thus, a series of 2-dimensional images may be acquired, but all of the images are substantially parallel with each other. Due to the inability to develop a 2-dimensional image between detectors 20 in rings more than one ring away, 3-dimensional imaging is not possible. The basic advantage of producing a 2-dimensional image as opposed to a 3-dimensional image is that a 2-dimensional image is much less time consuming and, thus, less expensive. However, with advances that are being made in the computational processing time, the derivation of 3-dimensional images is becoming more readily available.

The approach to acquiring transmission attenuation data using the present invention involves using a point source transmission and acquiring the data in a "singles" mode. Instead of using coincidences, as used in the prior art, to determine the LOR chords, the chords are described by the points of the detected event determined by detectors opposite the patient from the source, and the location of the source. Because of the sensors (e.g., 54,56), the position of the source can be accurately located. Then, given the location of these two points in a three dimension space, the chord is accurately described. By collecting data in this mode, the detector system is not paralyzed by the dead time losses of the detector adjacent to the transmission source as is the case when requiring transmission data in the prior coincidence method. The configuration, as described, not only provides an acquisition system more sensitive for a given amount of radiation activity than using the coincidence system, but permits using a radiation source having a significantly increased specific activity with a resulting increase in acquired counts. This results in substantially reduced acquisition time. This increase in activity is permitted since detectors adjacent the source, which will be paralyzed by the activity, are not used for establishing an end of the LOR chords as in the prior art.

In a further embodiment, the point source of radiation is a CT device mounted on a single rotational support with the PET or SPECT device. Specifically, a bank of CT detectors is placed within a gap defined between two bamks of detector units 20. A CT generator (X-ray generator) is positioned on the opposite side of the ring to direct X-rays through the patient to the bank of CT detectors. The CT device is moved about the patient 23 in a conventional fashion along with the PET detector banks and attenuation correction data is collected as in the previously described embodiments. However, CT scanning devices provide correction factors at lower energies (i.e., 40–120 keV as compared to 511 keV) than those desired. In order to accommodate for correction factors obtained from the CT scan, the correction factors obtained from the CT scan are scaled to achieve the appropriate strength. Any of several scaling methods may be used in order to accomplish this task. Of the scaling methods are: (1) simple global scaling based on the ratio of attenuation for water at the two energies (the obtained energy level and the desired energy level); (2) implementation of a CT device having dual energy capability, whereby scaling is actually unnecessary; (3) segmentation of the reconstructed CT image obtained from the scan into different regions such as tissue, bone and lungs, and using appropriate attenuation coefficients to scale data in each region; and (4) a hybrid of methods (1) and (3) above. For method (3), an exemplary scale factor is approximately 2.26 for bone regions and 1.85 for non-bone regions.

It will be understood that any other conventional device for obtaining anatomical data may be used in lieu of the CT scanner as described, as any other conventional device for obtaining functional data may be used in lieu of the PET or SPECT scanner. Because the two types of devices are mounted on a common rotational support, anatomical and functional data sets obtained therefrom are closely aligned. Therefore, registration of the two data sets is accomodated, while eliminating problems which arise when the two scans are performed using two separate scanners.

From the foregoing, it will be understood by persons skilled in the art that an improvement has been made to the manner of determining attenuation data in a positron emission tomograph unit. Further, while providing data of attenuation through a body for PET scanning, the system can be used to determine overall response of radiation detectors of the basic PET system.

The present invention has been described in detail as applied to positron emission tomograph (PET) units for illustration purposes. Due to the ability of the method and apparatus to rapidly move a point source of radiation in a selected 2-D or 3-D geometry, and to determine the position of that source, the present invention is applicable to various tomography applications. Further, the present invention is applicable for producing 2-D and 3-D transmission measurement images in any selected geometry and for any desired utilization of such images.

Although certain specific materials are recited herein, these are for illustrative purposes and not for limiting the invention. Accordingly, the invention is to be limited only by the appended claims and equivalents thereof when read together with the complete description of the present invention.

We claim:

1. A method for forming at least one of a multi-dimensional attenuation data set and an image of radiation transmission through an object positioned in a tomograph device, said tomograph device being at least one of a positron emission tomography (PET) device and a single photon emission computed tomography (SPECT) device, said tomograph device having radiation detectors defining a plurality of faces of said radiation detectors, said method comprising:

positioning a selected point source of radioactive radiation proximate each of said radiation detectors in a selected sequence, said radioactive radiation being directed through the object and received by said radiation detectors of said tomograph device; and processing signals received from outputs of said detectors of said tomograph device to determine transmission data of radiation from said source of radiation during passage of said radiation through the object for forming said at least one of an attenuation data set and an image.

2. The method of claim 1 further comprising detecting the location of said source of radiation.

3. The method of claim 1 wherein said tomograph device includes a plurality of collimators positioned between each consecutive pair of rings comprised of said radiation detectors, said at least one of a multi-dimensional attenuation data set and said image being two-dimensional.

4. The method of claim 1 wherein lines of response defined between pairs of said radiation detectors in uncommon rings comprised of said radiation detectors are unobstructed, said at least one of a multi-dimensional attenuation data set and an image being three-dimensional image.

5. A method for forming at least one of a multi-dimensional attenuation data set and an image of radiation transmission within an object positioned in a tomograph device, said tomograph device being at least one of a positron emission tomography (PET) device and a single photon emission computed tomography (SPECT) device, said tomograph device having radiation detectors defining a plurality of faces of said radiation detectors, said method comprising:

forming a conduit from tubing, said tubing having a selected interior diameter, said conduit having a configuration so as to have a portion positioned adjacent each of said plurality of radiation detector faces, said conduit having an inlet and an outlet;

filling said conduit with a transport fluid;

pumping said transport fluid within said conduit with a pump, said pump having an inlet and an outlet, said pump inlet being in fluid communication with said outlet of said conduit;

positioning a selected point source of radioactive radiation within said tubing of said conduit for circulating through said conduit by circulating said transport fluid, said radioactive radiation being directed through the object and received by said detectors of said tomograph device;

storing said point source of radiation within a storage shield when not being circulated through said conduit, said storage shield having an outlet in fluid communication with said inlet of said conduit and an inlet in fluid communication with said outlet of said pump; and processing signals received from outputs of said detectors of said tomograph device to determine transmission data of radiation from said source of radiation during passage of said radiation through the object.

6. The method of claim 5 further comprising detecting the location of said source of radiation within said conduit and within said shield.

7. The method of claim 5 wherein said tomograph device includes a plurality of collimators positioned between each consecutive pair of rings comprised of said radiation detectors, said at least one of a multi-dimensional attenuation data set and an image being two-dimensional.

8. The method of claim 5 wherein lines of response defined between pairs of said radiation detectors in uncommon rings comprised of said radiation detectors are unobstructed, said at least one of a multi-dimensional attenuation data set and an image being three-dimensional.

9. A system for forming at least one of a multi-dimensional attenuation data set and an image of radiation transmission within an object positioned in a tomograph device, said tomograph device being at least one of a positron emission tomography (PET) device and a single photon emission computed tomography (SPECT) device, said tomograph device having radiation detectors defining a plurality of faces of said radiation detectors, said system comprising:

a conduit formed from cylindrical tubing, said tubing having a selected interior configuration, said conduit having an external configuration so as to have a portion positioned adjacent at least a selected portion of said plurality of radiation detector faces, said conduit having an inlet and an outlet;

a transport fluid contained within said conduit;

a pump for circulating said transport fluid within said conduit, said pump having an inlet and an outlet, said pump inlet being in fluid communication with said outlet of said conduit;

a selected point source of radioactive radiation positioned within said tubing for circulating through said conduit by circulation of said transport fluid, said radiation directed through the object and received by said detectors of said tomograph device;

storage shield for containing said source of radioactivity when not being circulated through said conduit, said storage shield having an inlet in fluid communication with said outlet of said conduit and an outlet in fluid communication with said inlet to said pump; and signal processing circuitry connected to outputs of said detectors of said tomograph device to determine transmission data of radiation from said source of radiation during passage of said radiation through the object.

10. The system of claim 9 further comprising further processing circuitry connected to said outputs of said detectors of said tomograph device and to said signal processing circuitry to apply said transmission data to of said radiation source to data of annihilation photon transmission from within the object to said detectors of said tomograph device.

11. The system of claim 9 further comprising first and second detection units positioned proximate selected locations along said conduit to monitor for a presence of said source of radiation within said conduit between said selected locations.

12. The system of claim 11 wherein sensors of said detection units are connected to said pump to repetitively reverse pumping directions of said transport fluid whereby said source of radiation moves in an oscillatory direction within said conduit between said selected locations of said first and second detection units.

13. The system of claim 9 wherein said source of radiation is spherical and has a diameter to be closely received within said interior configuration of said tubing of said conduit.

14. The system of claim 9 wherein said source of radiation is cylindrical and has a diameter to be closely received within said interior configuration of said tubing of said conduit.

15. The system of claim 9 wherein said pump is a peristaltic pump for circulating said transport fluid through said conduit.

16. The system of claim 11 further comprising a further detection unit positioned at said storage shield to ascertain presence of said source of radiation within said storage shield.

17. The system of claim 16 further comprising a physical stop within said storage shield proximate said further detection unit to selectively hold said source of radiation within said storage shield in the absence of operation of said pump.

18. The system of claim 9 further comprising disconnect units at said inlet and outlet of said storage shield whereby said storage shield means containing said source of radiation can be disconnected from said conduit and said pump.

19. The system of claim 9 wherein said transport fluid is a hydraulic fluid having a specific gravity less than that of said source of radiation.

20. The system of claim 9 wherein said at least one of a multi-dimensional attenuation data set and an image of said radiation transmission is three-dimensional wherein lines of response are defined between pairs of said radiation detectors disposed in uncommon rings comprised of said radiation detectors are substantially unobstructed.

21. The system of claim 9 wherein said at least one of a multi-dimensional attenuation data set and an image of said radiation transmission is two-dimensional and wherein said system further includes a plurality of collimators between respective pairs of rings comprised of said radiation detectors.

* * * * *